US00PP10561P

United States Patent [19]

Elsner

[11] Patent Number: Plant 10,561

[45] Date of Patent: Aug. 18, 1998

[54] VARIETY OF GERANIUM NAMED 'DRAPIN'

[75] Inventor: Wilhelm Elsner, Dresden, Germany

[73] Assignee: Elsner Pac Jungpflanzen, Germany

[21] Appl. No.: 746,423

[22] Filed: Nov. 8, 1996

[51] Int. Cl.[6] ..... A01H 5/00

[52] U.S. Cl. ..... Plt./87.12

[58] Field of Search ..... Plt./87.12

[56] References Cited

PUBLICATIONS

UPOV CD-ROM 97/03 Plant Breeders Rights for 'Orapin' (PBR 97009), 1997.

*Primary Examiner*—James R. Feyrer

*Assistant Examiner*—Melissa L. Kimball

*Attorney, Agent, or Firm*—Webb Ziesenheim Bruening Logsdon Orkin & Hanson, P.C.

[57] ABSTRACT

The new cultivar is an early, continuous flowering variety. Its elegant coral red flowers have big umbels and continuously flower. It demonstrates good garden performance and greenhouse propagation. It also has a medium mound habit with more controlled and uniform growth for bench run finishing. The new cultivar is an improvement in comparison to the variety "Sunbelt Coral."

1 Drawing Sheet

BACKGROUND OF THE INVENTION

The present invention comprises a new and distinct cultivar of *Pelargonium×hortorum* known by the varietal name "Orapin" in the United States and marketed as "Northern Lights" outside the United States. The new cultivar was discovered at Elsner pac Jungpflanzen in Dresden, Germany, in November 1988. The new variety was discovered as a selection from a meristem propagation of the unpatented Orangepen cultivar. The new variety was first asexually reproduced by cuttings at Oglevee, Ltd. in Connellsville, Pa., in January 1994. It has also been trial and field tested at Elsner pac Jungflanzen in Dresden, Germany, and at Oglevee, Ltd. in Connellsville, Pa., and has been found to retain its distinctive characteristics through successive propagations.

The plant history has taken on six-week plants blossomed under the natural light in a greenhouse in 10 cm pots. The cultivar when grown in a glass greenhouse was potted on Feb. 13, 1996 and flowered on Mar. 25, 1996.

DESCRIPTION OF THE DRAWING

The accompanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics was collected from asexual reproductions carried out by Oglevee, Ltd. in Connellsville, Pa. The plant history was taken on six-week plants blossomed under natural light in a greenhouse and the color readings were taken indoors under 200–220 footcandles of cool white fluorescent light. Color references are primarily to the R.H.S. Colour Chart of The Royal Horticultural Society of London.

The Plant

Classification:

*Botanical.*—*Pelargonium×hortorum.*

*Commercial.*—Florists' zonal geranium.

*Form.*—Uniform, medium mound.

*Height.*—14.0–15.5 cm from soil line.

*Growth.*—Free basal branching.

*Strength.*—Stands upright without artificial support.

*Foliage.*—Stalked leaf attachment.

Leaves:

*Size.*—8.5–9.0 cm.

*Shape.*—Reniform.

*Margin.*—Crenate.

*Texture.*—Slightly reflective, slightly pubescent.

*Color.*—Top: Green group 137B. Bottom: Green group 138B.

*Zone.*—No prominent zone.

Ribs and veins:

*Venation.*—Palmate.

*Color.*—Green group 143C.

Petioles:

*Color.*—Yellow-green group 144A.

*Length.*—4.7–7.6 cm.

Stem:

*Color.*—Yellow-green group 144A with "speckling" of greyed-purple group 185A.

*Internodes.*—3.5–5.0 cm in length.

The Bud (Umbel)

Shape: Upright hemispherical clusters.

Size (diameter): 4.2–5 cm across, just cracking color.

Inflorescence

Blooming habit: Continuous and early flowering.

Size (diameter): 8.0–10.0 cm, fully open bloom.

Borne: Umbel, floret on pedicel, pedicel on peduncle, flowers 7.5–9.0 cm above the foliage.

Florets:

*Form.*—Cupped with ruffled appearance due to petaloids.

*Closed size.*—0.5–1.2 cm, just cracking color.

*Color.*—Top: Red group 40B. Bottom: Red group 41C with lighter streaking of red group 39C.

Petals:

*Quantity.*—6–7.
*Size.*—1.6–2.0 cm across.
*Texture and appearance.*—Smooth, slightly reflective.
Petaloids:
*Quantity.*—3–4.
*Shape.*—Irregular, ruffled, elliptical.
*Color.*—Top: Red group 40B. Bottom: Red group 41C.
Pedicel:
*Color.*—Greyed-purple group 185A with yellow-green group 144B.
*Length.*—1.5–3.5 cm.
Peduncle:
*Color.*—Yellow-green group 144A with greyed-purple group 185A.
*Length.*—13.0–18.5 cm.
Disease resistance: Not known.

Reproductive Organs

Stamens:
*Anthers.*—2.0–3.0 mm.
*Filaments.*—Length: 5.0–8.0 mm. Color: White.
*Pollen.*—Golden brown.
Pistils:
*Number.*—1, 5 parted.
*Length.*—7.0–8.0 mm.
*Stigma.*—Color: Orange to purple-red.
*Style.*—Length: 2.0–3.0 mm.
*Ovaries.*—Characteristics: Superior, slightly pubescent. Length: 4.0–5.0 mm. Color: Green.
Fruit: None observed.

General Characteristics

1. Medium mound habit is more controlled and uniform for bench run finishing.

2. Flowers earlier and more evenly.

3. Elegant flowers, big umbels and continuous flowering.

4. Good greenhouse production with regard to the number of cuttings and rooting ability.

5. Good outdoor performance.

6. Comparable inflorescence color to "Sunbelt Coral" (U.S. Plant Pat. No. 5,757) but about one third to one half the height of "Sunbelt Coral" with petioles, buds and florets about one half size of those of "Sunbelt Coral". The slightly reflective leaves are more green than the leathery leaves of "Sunbelt Coral".

I claim:

1. A new and distinct variety of geranium plant substantially as shown and described.

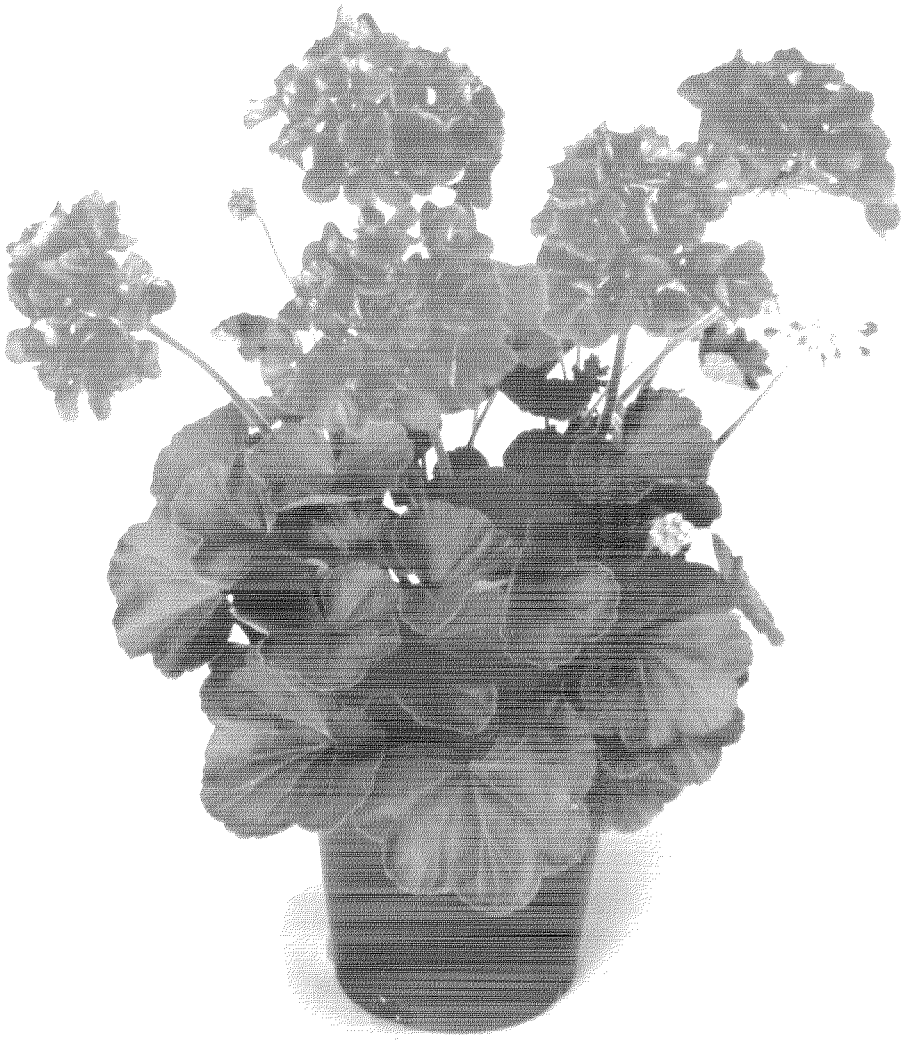

* * * * *